(12) United States Patent
McInally et al.

(10) Patent No.: US 9,045,472 B2
(45) Date of Patent: Jun. 2, 2015

(54) IMIDAZOQUINOLINE COMPOUNDS

(75) Inventors: Thomas McInally, Loughborough (GB); Austen Pimm, Macclesfied (GB)

(73) Assignees: ASTRAZENECA AB, Sodertalje (SE); SUMITOMO DAINIPPON PHARMA CO., LTD., Osaka (JP)

( * ) Notice: Subject to any disclaimer, the term of this patent is extended or adjusted under 35 U.S.C. 154(b) by 455 days.

(21) Appl. No.: 13/327,970

(22) Filed: Dec. 16, 2011

(65) Prior Publication Data

US 2012/0189646 A1    Jul. 26, 2012

Related U.S. Application Data

(60) Provisional application No. 61/423,644, filed on Dec. 16, 2010.

(51) Int. Cl.
C07D 471/04    (2006.01)
A61K 31/4745   (2006.01)

(52) U.S. Cl.
CPC ................................. C07D 471/04 (2013.01)

(58) Field of Classification Search
USPC ............................................ 546/82; 514/293
See application file for complete search history.

(56) References Cited

U.S. PATENT DOCUMENTS

| | | | |
|---|---|---|---|
| 4,179,562 A | 12/1979 | Ponsford | |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,541,485 B1 | 4/2003 | Crooks et al. | |
| 6,630,478 B2 | 10/2003 | Diamond et al. | |
| 6,951,866 B2 | 10/2005 | Fujita et al. | |
| 7,157,465 B2 | 1/2007 | Isobe et al. | |
| 7,642,350 B2 | 1/2010 | Pryde | |
| 7,754,728 B2 | 7/2010 | Isobe et al. | |
| 8,148,371 B2 | 4/2012 | Isobe et al. | |
| 2002/0040032 A1 | 4/2002 | Glasky et al. | |
| 2002/0068745 A1 | 6/2002 | Levy et al. | |
| 2002/0128264 A1 | 9/2002 | Taylor | |
| 2003/0144283 A1 | 7/2003 | Coleman et al. | |
| 2003/0191086 A1 | 10/2003 | Hanus et al. | |
| 2003/0212092 A1 | 11/2003 | Heppner et al. | |
| 2004/0019048 A1 | 1/2004 | Crooks et al. | |
| 2004/0132748 A1 | 7/2004 | Isobe et al. | |
| 2004/0214192 A1 | 10/2004 | Hashida et al. | |
| 2004/0229897 A1 | 11/2004 | Crooks et al. | |
| 2005/0054590 A1 | 3/2005 | Averett | |
| 2005/0119273 A1 | 6/2005 | Lipford et al. | |
| 2006/0052403 A1 | 3/2006 | Isobe et al. | |
| 2006/0252774 A1 | 11/2006 | Vatner | |
| 2007/0190071 A1 | 8/2007 | Kurimoto et al. | |
| 2007/0225303 A1 | 9/2007 | Ogita et al. | |
| 2008/0008682 A1 | 1/2008 | Chong et al. | |
| 2008/0269240 A1 | 10/2008 | Hashimoto et al. | |
| 2008/0300244 A1 | 12/2008 | Bonnert et al. | |
| 2009/0047249 A1 | 2/2009 | Graupe et al. | |
| 2009/0082332 A1 | 3/2009 | Abbot et al. | |

(Continued)

FOREIGN PATENT DOCUMENTS

| | | |
|---|---|---|
| CA | 1220148 | 4/1987 |
| CN | 101239980 | 8/2008 |

(Continued)

OTHER PUBLICATIONS

"Asthma", (MDAdvice.com) www.madadvice.com/topics/asthma/info, downloaded from the internet Oct. 19, 2010.
"Chronic Obstructive Pulmonary Disease" (AllRefer.com) www.health.allrefer.com/health/chronic-obstructive-pulmonary-disease-prevention. downloaded from the internet on Oct. 19, 2010.
"Respiratory Experts Call for Global Approach to Treat Chronic Disease", European Respiratory Society, Feb. 13, 2007: www.medwire-news.md/48/6443/Respiratory/Respiratory-experts-call-for-global-approach-to-treat-chronic-disease, downloaded from the internet on Oct. 19, 2010.

(Continued)

Primary Examiner — Rita Desai
(74) Attorney, Agent, or Firm — Finnegan, Henderson, Farabow, Garrett & Dunner LLP

(57) ABSTRACT

Disclosed herein are a compound of formula (I) and pharmaceutically acceptable salts thereof, processes for preparing the same, pharmaceutical compositions containing the same, and methods of using the same.

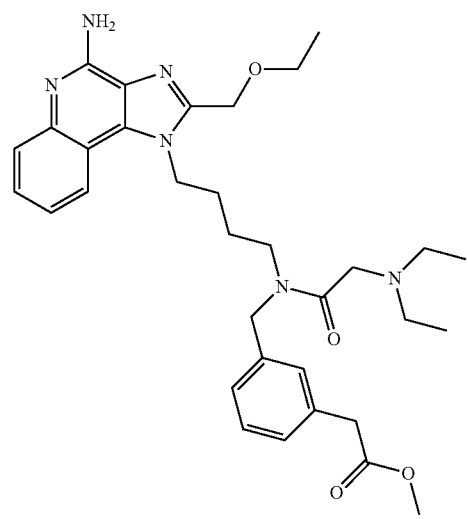

12 Claims, 2 Drawing Sheets

(56) References Cited

U.S. PATENT DOCUMENTS

| | | |
|---|---|---|
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0264447 A1 | 10/2009 | Dietz et al. |
| 2009/0281075 A1 | 11/2009 | Roughton et al. |
| 2009/0324551 A1 | 12/2009 | Carson et al. |
| 2009/0325877 A1 | 12/2009 | Grunt et al. |
| 2010/0075995 A1 | 3/2010 | Biggadike et al. |
| 2010/0087433 A1 | 4/2010 | Bomont et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2010/0280001 A1 | 11/2010 | Bonnert et al. |
| 2010/0296364 A1 | 11/2010 | Pensler et al. |
| 2011/0136801 A1 | 6/2011 | Isobe et al. |
| 2012/0122867 A1 | 5/2012 | Bennet et al. |

FOREIGN PATENT DOCUMENTS

| | | |
|---|---|---|
| EP | 1035123 | 9/2000 |
| EP | 1 110 951 | 6/2001 |
| EP | 1 541 572 | 6/2005 |
| EP | 1 550 662 | 7/2005 |
| EP | 1 728 793 | 12/2005 |
| GB | 1375162 | 11/1974 |
| JP | 08-165292 | 6/1995 |
| JP | 10-501533 | 2/1998 |
| JP | 10-507171 | 7/1998 |
| JP | 11/180981 | 7/1999 |
| JP | 11-180982 | 7/1999 |
| JP | 11-193282 | 7/1999 |
| JP | 2000-159767 | 6/2000 |
| JP | 2004-137157 | 5/2004 |
| JP | 2005-089334 | 4/2005 |
| WO | WO 98/01448 | 1/1993 |
| WO | WO 99/32122 | 7/1999 |
| WO | WO 99/28321 | 10/1999 |
| WO | WO 99/50249 | 10/1999 |
| WO | WO 00/12487 | 3/2000 |
| WO | WO 00/76505 | 12/2000 |
| WO | WO 00/76519 | 12/2000 |
| WO | WO 01/007027 | 2/2001 |
| WO | WO 01/27131 | 4/2001 |
| WO | WO 02/04449 A2 | 1/2002 |
| WO | WO 02/46193 | 6/2002 |
| WO | WO 02/085905 | 10/2002 |
| WO | WO 03/011864 | 2/2003 |
| WO | WO 2004/011481 | 2/2004 |
| WO | WO 2004/029054 A1 | 4/2004 |
| WO | WO 2004/075865 | 9/2004 |
| WO | WO 2004/087049 | 10/2004 |
| WO | WO 2005/009978 | 2/2005 |
| WO | WO 2005/025583 | 3/2005 |
| WO | WO 2005/092892 | 10/2005 |
| WO | WO 2005/092893 | 10/2005 |
| WO | WO 2006/029115 | 3/2006 |
| WO | WO 2006/091394 | 8/2006 |
| WO | WO 2006/117670 | 11/2006 |
| WO | WO 2006/129784 | 12/2006 |
| WO | WO 2006/137706 | 12/2006 |
| WO | WO 2007/031726 | 3/2007 |
| WO | WO 2007/031829 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008/001070 | 1/2008 |
| WO | WO 2008/004948 | 1/2008 |
| WO | WO 2008/015250 | 2/2008 |
| WO | WO 2008/071976 | 6/2008 |
| WO | WO 2008/083465 | 7/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009/067061 | 5/2009 |
| WO | WO 2009/078798 | 6/2009 |
| WO | WO 2009/091031 | 7/2009 |
| WO | WO 2009/091032 | 7/2009 |
| WO | WO 2010/133882 | 11/2010 |
| WO | WO 2011/068233 | 6/2011 |
| WO | WO 2012/066335 | 5/2012 |
| WO | WO 2012/066336 | 5/2012 |
| WO | WO 2012/067269 | 5/2012 |

OTHER PUBLICATIONS

Aoki, M. et al., "Weekly Dosing of AZD8848/DSP-3025, A Novel TLR7 Agonist Antedrug, Demonstrates a Prolonged Period of Control Against Markers of Pulmonary Inflammation in an Allergen Challenge Model in the Mouse", ATS, New Orleans. May 2010.

Baichen, T., et al., .Pharmacokinetics, Safety and Tolerability of Single Ascending Intranasal Doses of AZD8848 in BChE-Deficient Volunteers, American Thoracic Society, San Francisco, May 18-23, 2012.

Bell, J., "AZD8848/DSP-3025, A Novel Potent TLR7 Agonist Antedrug, Demonstrates Negligible Systemic Activity and a Prolonged Period of Control After Cessation of Weekly Dosing in a Brown Norway Rat Ovalbumin Challenge Model", ATS, New Orleans, May 2010.

Biffen, M, et al., "Novel TLR7 Agonists for the Treatment of Allergic Diseases", Toil 2011, Riva del Garda, Italy, May 4-7, 2011.

Biffen, M., et al., "Biological Activity of a Novel TLR7 Agonist Antedrug For the Treatment of Allergic Diseases", ATS, New Orleans, May 2010.

Biffen, M., et al., "Biological Characterization of a Nova Class of Toll-Like Receptor 7 Agonists Designed to Have Reduced Systemic Activity", British Journal of Pharmacology, 166 (2012) pp. 573-586.

Chavarot, M., et al., "Synthesis of an Adenine-Pyridinaldoxime-Acridine Conjugate for Recognition of Abasio Site Lesins in DNA", Tetrahedron, vol. 53, No. 40 (1997) pp. 13749-13756.

Drazer, M., "Surgery for Emphysema—Not for Everyone", The New England Journal of Medicine, vol. 345, No. 15, Oct. 11, 2001; pp. 1126-1128.

Dvorakova, H., et al, "Synthesis of 2'-Aminomethyl Derivatives of N-(2-(Phosphonomethoxy) Ethyl) Anaioques as Potential Antiviral Agents", J. Med, Chem. 39 (1996) pp. 3263-3268.

Eiho, K., et al., "Mechanism of Long-Lasting Suppression Against TH2 Immune Response in the Lung by a Novel Antedrug TLR7 Agonist", European Respiratory Society, Amsterdam, Sep. 24-28, 2011.

English translation of Japanese Patent Application No. 347422/1997.
English translation of Japanese Patent Application no. 367449/1997.
English translation of Japanese Patent Application No. 367451/1997.

Falco, E.A., et al., "2,4-Diaminopyrimidines as Antimalarials. I. 5-Aroyloxyl and 5-Alkexyl Derivatives", Journal of the American Chemical Society, vol. 73. No. 8 (1951) pp. 3753-3758.

Fridkin, Scott K., "Vancomycin-Intermediate and Resistant *Staphylococcus aureus*: What the Infectious Disease Specialist Needs to Know" Healthcare Epidemiology vol. 32 (2001) pp. 108-115.

Gorden, K.B., et al., Syntheic TLR Agonists Reveal Functional Differences Between Human TLR7 and TLR8, The Journal of Immunology 174 (2005) pp. 1259-1268.

Greiff, et al., "Efficacy and Tolerability of the Toll-like Receptor 7 (TLR7) Agonist AZD8848 in Patients with Seasonal Allergic Rhinitis", American Thoracic Society, San Francisco, May 18-23, 2012.

(56) References Cited

OTHER PUBLICATIONS

Greiff, L., et al., "Repeated Intranasal TLR7 Stimulation Reduces Allergen Responsiveness in Allergic Rhinitis", Respir Res. Jun. 22, 2012: 13(1):53.
Greiff, L., et al.. Repeated Intranasal TLR7 Stimulation Reduces Allergen Responsiveness in Allergic Rhinitis, European Respiratory Society Amsterdamn, the Netherlands Sep. 24-28. 2011.
Hirota. K., et al., "Discovery of 8-Hydroxyadenines as a Novel Type of Interferon Inducer", J. Med. Chem, (2002) pp. 5419-5422.
Holy, A. et al.,"9-(Arninoalykyl)-8-Hydroxyadenines: Preparation; Mechanism of Formation and Use in Affinity Chromatography of S-Adenosyl-L-Homocysteine Hydrolase" Collection of Czechoslovak Chem. Commun. vol. 51 (1986) pp. 459-477
Huber, J.P., et al,, "Cutting Edge: Type I Ifn Reverses Human Th2 Commitment and Stability by Suppressing GATA3", the Journal of Immunology 185. (2010) pp. 813-817.
Ikeda. K., et al,, "AZD8848/DSP-3025, A Novel Poent TLR7 Agonist Antedrug, Demonstrates Efficacy Against Airway Obstruction and Other Inflammatory Endpoints in Guinea Pig Models of Rhinitis and Asthma with Acute and Weekly Dosing", ATS, New Orleans, May 2010.
lsobe, Y., et al., "Synthesis and Biological Evaluation of Novel 9-Substituted-8-Hydroxyadenine Derivatives as Potent Interferon Inducers", J. Med. Chem 49 (2006) pp. 2088-2095.
lsobe, Y., et al., "Synthesis and Structure-Activity Relationships of 2-Substituted-8-hydroxyadenine Derivatives as Orally Available Interferon inducers without Emetic Side Effects", Biorganic & Medicinal Chemistry, vol. 11, Issue 17 (20032001) pp. 3641-3647
Ithara,T., et al., "Control of Liguid-Crystalline", ChemPhysChein, No. 4 (2002) pp, 378-379.
Korc, M., "Pathways for Aberrant Angiogenesis in Pancreatic Cancer", Molecular Cancer BioMed Central., vol. 2 (2003) pp. 1-8.
Krueger, Russell, F., et al.,"Tilorone Hydrochloride: an Orally Active Antiviral Agent", Science, vol. 159, Sep. 18, 1970, pp. 1213-1215.
Kuhn, Wolfgang, et al., Impact of Dose and Dosing Frequency of Intranasal AZD8848 (a TLR7 agonist) on Biomarker Response in Healthy Volunteers, American Thoracic Society, San Francisco; May 18-23, 2012.
Kurimoto, A. et al., "Synthesis and Evaluation of 2-substituted 8-hydroxyadenines as Potent Interferon inducers with Improved Oral Bioavailabilities", Bioorganic & Medicinal Chemistry 12 (2004) pp. 1091-1099.
Kurimoto, A. et al., "Synthesis and Structure—Activity Relationships of 2-Amino-8-hydroxyadenines as Orally Active Interferon Inducing Agents", Bioorganic & Medicinal Chemistry 11 (2003) pp. 5501-5508.
Kurimoto, A., et al., Synthesis and Biological Evaluation of 8-Oxoadenine Derivatives as Toll-like Receptor 7 Agonists Introducing the Antedrug Concept, Journal of Medicinal Chemistry, vol. 53, No. 7 (2010) pp. 2964-2972.
Kurimoro, A et al., Prodrugs of 9-Benzyl-8-hydroxy-2-(2-hydroxyethylthio)adenine: Potent Interderon Inducing Agents in Monkeys, Chem. Pharm. Bull. vol. 52, No. 4 (2004) pp. 466-469.
Laino, C., "In Small Study, Imaging Detects Lung Damage in People Exposed to Secondhand Smoke", Oncology Times, vol. 30, issue 2, Jan. 25, 2008, pp. 1-3.
Leaker, B., et al the Effects of the Novel Toll-like Receptor 7 (TLR7) Agonist AZD8848 on Allergen-Induced Responses in Patients with Mild Asthma, American Thoracic Society, San Francisco, May 18-23, 2012.
Leaker, B., et al. The Effects of the Novel Toll-like Receptor 7 (TLR7) Agonist AZD8848 on Allergen-Induced Responses in Patients with Mild Asthma, European Respiratory Society, Vienna, Sep. 1-5, 2012.
Lee, J. et al., "Molecular Basis for the Irnmunostimulatory Activity of Guanine Nucleoside Analogs: Activation of Toll-like Receptor 7", Proceedings of the National Academy of Sciences USA, vol. 11, No. 100. May 27, 2003, pp. 6646-6651.
Lee, J., et al., "Activation of Anti-Hepatitis C Virus Responses via Toll-like Receptor 7", Proceedings of the National Academy of Sciences USA, vol. 103, No. 6. Feb. 7, 2006, pp. 1828-1833.
Matsui, H., "Mechanisms of Inhibition of Type-2 Cytokines by Novel TLR7 Agonist Antedrugs", ATS New Orleans, May 2010.
Matsui, H., et al., "Mechanism of Action of Inhibition of Allergic Immune Responses by a Novel Antedrug TLR7 Agomst," The Journal of Immunology, vol. 189, No. 11, Nov. 2, 2012, pp. 5194-5205.
Mayer, et al., "Tilorone Hydrochloride: Mode of Action", Science, vol. 169 (1970) pp. 1214-1215.
McInally. T., et al., "Identification and Pharmacology of Novel TLR7 Agonist Antedrugs", RSC BMSC Inflammation Meeting Nov. 18, 2010.
McInally, T., et al., Identification of a Novel TLR7 Agonist Antedrusr, Brussels, Belgium, Sep. 5-9, 2010.
Mogulkoc, N., et al., "Pulmonary Function in Idiopathic Pulmonary Fibrosis and Referral for Lung Transplantation". American Journal of Respiratory and Critical Care Medicine (2001), vol. 164 pp. 103-108.
Nichol, F,R., "Stimulation of Murine Interferon by a Substituted Pyrimidine", Antimicrobial Agents and Chemotherapy vol. 9, no. 3, Mar. 1967 pp. 433-439 '.
Palmer, S., et al , "Highly Drug-Resistant HIV-1 Clinical Isolates are Cross-Resistant to Many Antiretroviral Compounds in Current Clinical Development", Aids (1999) Vol, 13, No. 6 pp. 661-667.
Reiter, M.J., et al., "Cytokine Induction in Mice by the Immunomodulator Imiquimod", Journal of Leukocyte Biology , vol. 55, Feb. 1994, pp. 234-240.
Spassova, M., et al., "Synthesis of N-(3-Azido-2-Hydroxypropyl), N-(3-Fhthalirnido-2-Hydroxypropyl) and N(3-Amino-2-Hydroxypropyl) Derivatives of Heterocyclic Bases", Collect. Czech, Chem. Commun. vol. 59 (1994) pp. 1153-1174.
Stringfellow, D.A., "Antiviral and Interferon-Inducing Properties of 1,5-Diamino Anthraquinones", Antimicrobial Agents and Chemotherapy, vol. 15, No. 1, Jan. 1979, pp. 111-118.
Tarkoy, M. et al., Nucleic-Acid Analogues with Constraint Conformational Flexibility in the Sugar-Phosphate Backbone (Sicyclo-DNA'), Helvetica Chalice Acta, vol. 76, No. 1 (1993) pp. 481-510.
Toto, S., et al , "Synthesis and Biological Evaluation of a Novel TLR7 Agonist with an Antedrug Strategy", Brussels, Sep. 2010.
Yoshimoto, M., et al., "Correlation Analysis of Baker's Studies on Enzyme Inhibition. 2. Chymotrypsin, Trypsin, Thymidine Phosphorylase, uridine Phosphoryllas, Thymidylate Synthetase, Cytosine Nucleoside Deaminase, Dihysrofolate Reductase, Malate Dehydrogenase, Glutamate Dehydrogenase, Lactate Dehydrogenase, and Glyceraldehyde-phosphate Dehydrogenase", Journal of Medicinal Chemistry, vol. 19, No. 1 (1976) pp. 71-98.
Zaiutsky, M.R., "Targeted Radiotherapy of Brain Tumours", British Journal of Cancer (2004) pp. 1469-1473.
Examination Report for European Patent Application No. 11 805 574.8, dated Apr. 4, 2014, from the European Patent Office (5 pages).

IMIDAZOQUINOLINE COMPOUNDS

This application claims the benefit under 35 U.S.C. §119 (e) of Application No. 61/423,644 filed on Dec. 16, 2010.

The present application discloses the novel compound methyl (3-{[{4-[4-amino-2-(ethoxymethyl)-1H-imidazo[4,5-c]quinolin-1-yl]butyl}(N,N-diethylglycyl)amino]methyl}phenyl)acetate and pharmaceutically acceptable salts thereof, processes for preparing the same, pharmaceutical compositions comprising the same, and methods of using the same.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha (IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRRs, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in PCT Publication Nos. WO 98/01448 and WO 99/28321.

TLR7 agonists suppress the Th2 cell dependent immune response through enhancement of the Th1 response. Such agonists are expected to be useful in the treatment of a number of diseases by modulating the Th1/Th2 immune response. However, systemic exposure to a TLR7 agonist may result in undesirable side-effects such as flu-like symptoms caused by induction of cytokines including IL-6, IL-12, and type I IFN.

PCT Publication No. WO 2008/135791 describes a class of imidazoquinoline compounds having immuno-modulating properties which act via TLR7 that are useful in the treatment of, for example, viral or allergic diseases and cancers.

The ester moieties in the compounds described in WO 2008/135791 may be quickly metabolised in plasma to the less active acid form. Those compounds are therefore suitable for topical administration and may be expected to exert the desired effects at the site of administration but quickly be converted to the less active acid metabolite upon entry into the systemic circulation, thereby reducing undesirable side effects which may be associated with systemic exposure to a TLR7 agonist.

PCT Publication No. WO 2008/135791 discloses 81 specific examples of compounds, salts and crystalline forms. Example 7 of WO 2008/135791 is the compound methyl 2-(3-((N-(3-(4-amino-2-(ethoxymethyl)-1H-imidazo[4,5-c]quinolin-1-yl)propyl)-2-(dimethylamino)acetamido)methyl)phenyl)acetate, which has a formula:

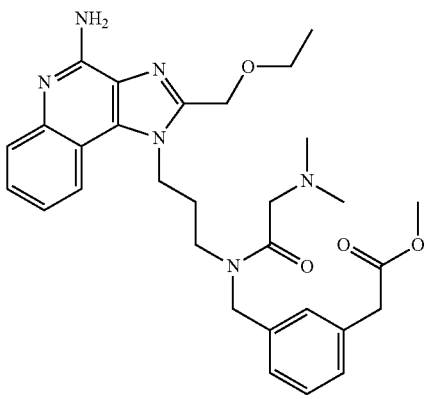 [SMILES: CCOCc1nc2c(N)nc3ccccc3c2n1CCCN(Cc1cccc(CC(=O)OC)c1)C(=O)CN(C)C]

WO 2008/135791 Example 7

The novel compound methyl (3-{[{4-[4-amino-2-(ethoxymethyl)-1H-imidazo[4,5-c]quinolin-1-yl]butyl}(N,N-diethylglycyl)amino]methyl}phenyl)acetate has now been prepared and found to be a potent TLR7 agonist. The compound has a number of desirable properties and, as such, is expected to be particularly suitable in the treatment of a number of conditions discussed hereinafter.

The structure of methyl (3-{[{4-[4-amino-2-(ethoxymethyl)-1H-imidazo[4,5-c]quinolin-1-yl]butyl}(N,N-diethylglycyl)amino]methyl}phenyl)acetate, formula (I), is shown below:

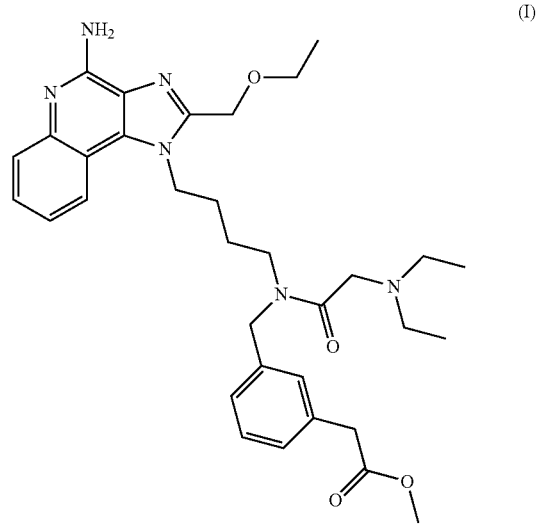 [SMILES: CCOCc1nc2c(N)nc3ccccc3c2n1CCCCN(Cc1cccc(CC(=O)OC)c1)C(=O)CN(CC)CC]

(I)

Disclosed herein is the novel compound of formula (I) (herein "Compound (I)") in the form of a free base, and pharmaceutically acceptable salts thereof. In an aspect of the disclosure, there is provided Compound (I). In another aspect of the disclosure, pharmaceutically acceptable salts of Compound (I) are provided.

Compound (I) and its pharmaceutically acceptable salts may exist in solvated (such as, for example, hydrated) as well as unsolvated forms. All solvated and unsolvated forms are encompassed herein.

Compound (I) may also exhibit polymorphism. It is to be understood that all polymorphic forms of Compound (I) are encompassed herein.

A suitable pharmaceutically acceptable salt of Compound (I) may be, for example, an acid-addition salt of Compound (I), such as an acid-addition salt with a suitable inorganic or organic acid. Examples of inorganic acid addition salts include hydrochloride, hydrobromide, sulfate, hydroiodide, nitrate, and phosphate. Examples of organic acid salts include oxalate, acetate, formate, propionate, benzoate, trifluoroacetate, fumarate, succinate, saccharin, maleate, citrate, lactate, tartrate, pyruvate, methanesulfonate, benzenesulfonate, and p-toluenesulfonate. The salt may be a non-stoichiometric or stoichiometric salt, such as a mono or di-salt, such as a monosaccharin or di-saccharin salt.

In the context of the present disclosure, the term "salt" means a crystalline material in which Compound (I) and an acid are ionized or, alternatively, where both components utilise prominent intermolecular interactions, such as hydrogen bonding, to combine and yield a uniform crystalline material (a co-crystal). It will be appreciated that a salt as disclosed herein may be partially ionic and partially co-crystal.

A further aspect of the disclosure provides a crystalline form of Compound (I) (herein "Compound (I) Form A"). Compound (I) Form A is crystalline and provides an X-ray powder diffraction (XRPD) pattern substantially as shown in FIG. 1 when measured at a wavelength of 1.5418 Å. The peaks (2θ values) of high intensity in the XRPD pattern for Compound (I) Form A are listed in Table 1. The °2θ values in Table 1 are measured to an accuracy of +/−0.1°.

TABLE 1

| Angle<br>2-Theta (2θ)° |
| --- |
| 5.3 |
| 7.6 |
| 9.3 |
| 10.7 |
| 11.6 |
| 12.4 |
| 13.0 |
| 13.2 |
| 13.8 |
| 14.5 |
| 15.2 |
| 15.6 |
| 15.9 |
| 16.9 |
| 17.8 |
| 18.2 |
| 18.5 |
| 19.7 |
| 20.0 |
| 20.5 |
| 20.8 |
| 21.3 |
| 21.8 |
| 22.2 |
| 22.8 |
| 23.4 |
| 24.1 |
| 24.8 |
| 25.2 |
| 26.1 |
| 26.6 |
| 27.9 |
| 30.2 |
| 31.0 |
| 31.8 |
| 32.3 |
| 33.0 |
| 33.4 |
| 34.1 |
| 35.6 |

TABLE 1-continued

| Angle<br>2-Theta (2θ)° |
| --- |
| 37.6 |
| 38.6 |

Compound (I) Form A may be prepared according to Example 1 hereinafter.

In some embodiments of the disclosure, the compound of formula (I) is Form A. In some embodiments of the disclosure, Compound (I) Form A has an X-ray powder diffraction pattern comprising at least one peak at a 2θ value selected from the 2θ values listed in Table 1+/−0.1°, when measured at a wavelength of 1.5418 Å.

In some embodiments of the disclosure, Compound (I) Form A has an X-ray powder diffraction pattern comprising at least two peaks (such as, for example, at least 2, 3, 4, 5, 6, 7, 8, 9 or 10 peaks) at 2θ values selected from the 2θ values listed in Table 1+/−0.1°, when measured at a wavelength of 1.5418 Å.

In some embodiments of the disclosure, Compound (I) Form A has an X-ray powder diffraction pattern substantially as shown in FIG. 1.

Compound (I) Form A is crystalline. In some embodiments, Compound (I) Form A may be substantially free from other crystalline and non-crystalline forms of Compound (I). For example, Compound (I) Form A may comprise less than 20%, 15%, 10%, 5%, 3%, or 1% by weight of other crystalline and/or non-crystalline forms of Compound (I).

In some embodiments, the degree of crystallinity of Compound (I) Form A, as determined by X-ray powder diffraction data, is greater than about 60%, such as greater than about 80%, greater than about 90%, or greater than about 95%. In some embodiments of the disclosure, the degree of crystallinity as determined by X-ray powder diffraction data may be greater than about 98%, wherein the degree of crystallinity refers to the fraction of crystalline material by weight of the total sample mass.

It is known in the art that an X-ray powder diffraction pattern may vary depending on measurement conditions (such as, for example, equipment, sample preparation and machine used). It is also known that intensities of peaks in an X-ray powder diffraction pattern may vary depending on, for example, measurement conditions and sample preparation. For example, persons skilled in the art of X-ray powder diffraction will realize that the relative intensities of peaks may vary according to the orientation of the sample under test and on the type and setting of the instrument used. Persons skilled in the art will also realize that the position of reflections can be affected by the precise height at which the sample sits in the diffractometer and the zero calibration of the diffractometer. The surface planarity of the sample may also have a small effect. Hence, a person skilled in the art will appreciate that the diffraction pattern data presented herein are not to be construed as absolute, and that any crystalline form that provides a powder diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

The present disclosure provides processes for the preparation of Compound (I) and pharmaceutically acceptable salts thereof.

In some embodiments, Compound (I) and pharmaceutically acceptable salts thereof are prepared according to Process (a). Process (a) comprises:

reacting a compound of formula (II) or a salt thereof:

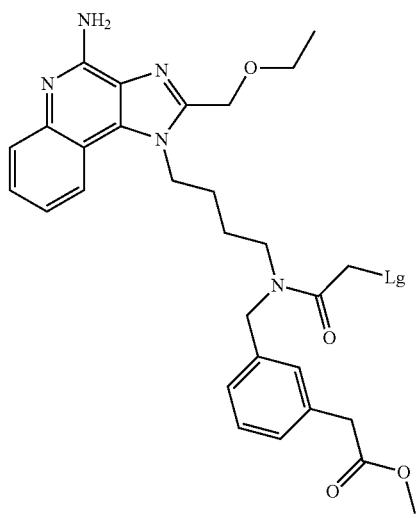
(II)

wherein Lg is a leaving group,
with diethylamine.

In some embodiments, Compound (I) and pharmaceutically acceptable salts thereof are prepared according to Process (b). Process (b) comprises:

coupling a compound of formula (III) or a salt thereof:

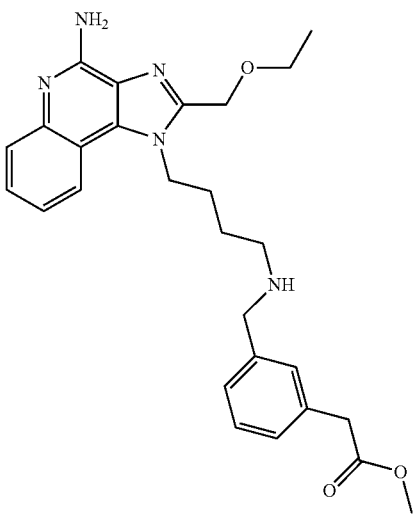
(III)

with 2-(diethylamino)acetic acid or a salt thereof.

Process (a) and Process (b) each independently optionally further comprises forming a pharmaceutically acceptable salt of the resulting Compound (I).

Process (a) Conditions:

Examples of leaving groups (Lg) in compounds of formula (II) include halo (for example chloro, bromo or iodo), mesylate (methylsulfonyloxy), triflate (trifluoromethanesulfonyloxy), besylate (benzenesulfonyloxy), and tosylate (toluenesulfonyloxy).

In some embodiments, the reaction may be carried out in the presence of a solvent, such as, for example, a polar aprotic solvent (such as tetrahydrofuran, dichloromethane, dimethylformamide and dimethylsulfoxide) or a non-polar organic solvent (such as toluene). In some embodiments, the reaction may be performed at a temperature ranging from room temperature to the reflux temperature of the reaction mixture, for example, the reaction may be performed at room temperature.

Compounds of formula (II) may be prepared by, for example, reacting a compound of formula (III) or a salt thereof as hereinbefore defined in relation to Process (b) with a compound of formula (IV):

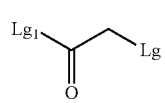
(IV)

wherein Lg and $Lg^1$ are independently selected leaving groups.

Leaving groups Lg and $Lg^1$ may be the same or different, provided that $Lg^1$ is more labile (easily removable) than Lg. Possible leaving groups are as hereinbefore defined in relation to Process (a). In some embodiments, $Lg^1$ is halo, for example, chloro. In one embodiment Lg and $Lg^1$ are both chloro.

In some embodiments, Compound (I) may be prepared directly from a compound of formula (III) by reacting compounds of formulae (III) and (IV) followed by a reaction of the product of that reaction with diethylamine, without isolating the compound of formula (II).

Process (b) Conditions:

In some embodiments, the coupling reaction of a compound of formula (III) or a salt thereof with 2-(diethylamino)acetic acid or a salt thereof may be carried out in the presence of a suitable coupling agent and, optionally, also in the presence of a suitable base. An example of a suitable coupling agent is O-(7-Azabenzotriazol-1-yl)-N,N,N',N'-tetramethyluronium hexafluorophosphate. A suitable base may be, for example, an organic amine base, such as triethylamine. In some embodiments, 2-(diethylamino)acetic acid is used in the form of a salt, for example a hydrochloride salt. In some embodiments, the coupling reaction may be carried out in the presence of a suitable solvent, for example, N,N-dimethylformamide or N-methylpyrrolidine, at a temperature, for example, ranging from 0° C. to 60° C., such as at room temperature.

Compounds of formula (III) and salts thereof may be prepared by reacting a compound of formula (V) or a salt thereof:

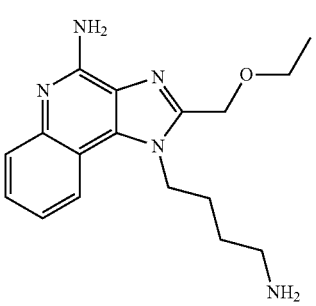
(V)

with methyl 2-(3-formylphenyl)acetate in the presence of a suitable reducing agent.

Examples of suitable reducing agents include hydride reducing agents, for example, alkali metal aluminium hydrides (such as lithium aluminium hydride) and alkali metal borohydrides (such as sodium borohydride, sodium cyanoborohydride, sodium triethylborohydride, sodium trimethoxyborohydride, and sodium triacetoxyborohydride). In some embodiments, the reducing agent is sodium cyanoborohydride.

The reaction of a compound of formula (V) or a salt thereof with methyl 2-(3-formylphenyl)acetate may be performed in a suitable inert solvent or diluent, for example, tetrahydrofuran or diethyl ether for strong reducing agents such as lithium aluminium hydride, and, for example, methylene chloride or a protic solvent such as methanol and ethanol for weaker reducing agents such as sodium triacetoxyborohydride and sodium cyanoborohydride.

The reaction may be performed at a temperature, for example, ranging from 0° C. to 100° C., such as from 0° C. to 40° C., or at or near room temperature. The reaction may optionally be carried out in the presence of an acid, for example, an organic acid, such as acetic acid.

In some embodiments, the compound of formula (V) may be in the form of a salt, for example a hydrochloride salt.

The compound of formula (V) may be prepared using methods known in the art, such as the methods described in the Examples herein.

It will be appreciated by those skilled in the art that, in the processes disclosed herein, certain functional groups, such as hydroxyl or amino groups, in the reagents may be protected by protecting groups. Thus, the preparation of Compound (I) may involve, at an appropriate stage, the removal of at least one protecting group.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The removal of any protecting groups and the formation of a pharmaceutically acceptable salt of Compound (I) may be performed using standard techniques known by persons of ordinary skill in the art. For example, a pharmaceutically acceptable salt of Compound (I) may be prepared by reacting Compound (I) with a suitable acid. Alternatively, well-known counter ion exchange methods may be used to convert one salt to another.

Certain intermediates used in the preparation of Compound (I) are novel, including compounds of formulae (II) and (III).

Thus, in an aspect of the disclosure, there is provided a compound of formula (II) and salts thereof as hereinbefore defined, for example, methyl (3-{[{4-[4-amino-2-(ethoxymethyl)-1H-imidazo[4,5-c]quinolin-1-yl]butyl}(chloroacetyl)amino]methyl}phenyl)acetate and salts thereof.

According to another aspect of the disclosure, there is provided a compound of formula (III) and salts thereof as hereinbefore defined, for example, methyl {3-[({4-[4-amino-2-(ethoxymethyl)-1H-imidazo[4,5-c]quinolin-1-yl]butyl}amino)methyl]phenyl}acetate and salts thereof.

The intermediates described herein may be used in the form of a salt. The salt may be a pharmaceutically acceptable salt, such as one of the salts mentioned hereinbefore in relation to Compound (I). Alternatively, the intermediates may be used in the form of a salt which is not a pharmaceutically acceptable salt. Such salts may be advantageously used in the synthesis of compounds according to the disclosure, for example as a result of advantageous physical and/or chemical properties, such as crystallinity.

Compound (I) and pharmaceutically acceptable salts thereof may have antedrug properties. An antedrug is an active synthetic derivative that is designed to undergo biotransformations to a readily-excretable, less active form upon entry into the systemic circulation, thereby minimizing systemic side-effects. Thus, on administration, a compound disclosed herein may be rapidly degraded enzymatically to yield a degradation product having a substantially reduced medical effect. A medical effect as used herein means a pharmacological activity, including specifically interferon inducing activity and/or suppression of IL-4/IL-5 production activity.

The medical effect of the degradation product may be, for example, 10 times, such as 100 times, less than that of the compound of disclosed herein (i.e. parent compound).

Pharmacological activity may be measured using methods known in the art, for example, using in vitro evaluation methods such as commercially-available ELISA kits and/or the biological assay described herein.

Diseases and Medical Conditions:

Compound (I) and pharmaceutically acceptable salts thereof disclosed herein may be useful as modulators of TLR7 activity and may provide an immuno-modulator effect. Compound (I) and pharmaceutically acceptable salts thereof thus are expected to be useful as therapeutic and prophylactic agents for diseases associated with an abnormal immune response (e.g. autoimmune diseases and allergic diseases) and/or various infections and cancers which are required for activation of an immune response. Compound (I) and pharmaceutically acceptable salts thereof may also be useful as vaccine adjuvants. For example, Compound (I) and pharmaceutically acceptable salts thereof may be administered to a mammal, including a human or a patient in need thereof, for the treatment of the following conditions or diseases:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, actinic keratosis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; hemangioma; pre-cancerous skin lesions; basal cell carcinoma, for example superficial basal cell carcinoma, nodular basal cell carcinoma and bowen's disease; cutaneous lymphomas, non-melanoma skin cancer and other dysplastic lesions; drug-induced disorders including fixed drug eruptions; skin scarring, including keloids; cutaneous infections, including viral cutaneous infections; cosmetic effects including photo-damaged skin;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial infections;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, chlamydia, candida, *aspergillus*, cryptococcal meningitis, *pneumocystis carnii*, cryptosporidiosis, histoplasmosis, toxoplasmosis, trypanosome infection and leishmaniasis.

Thus, the present disclosure provides methods of treating or reducing the risk of a disease or condition comprising administering to a patient in need thereof a therapeutically effective amount of Compound (I) and/or a pharmaceutically acceptable salt thereof.

In a further aspect, the present disclosure provides methods of making a medicament for use in treatment and/or therapy of a disease or condition, wherein said medicament comprises Compound (I) and/or a pharmaceutically acceptable salt thereof.

In the context of the present specification, the term "therapy" also includes "prophylaxis" unless indicated to the contrary. The terms "therapeutic" and "therapeutically" should be construed accordingly.

Prophylaxis may be relevant to the treatment of persons who have suffered a previous episode of, or are otherwise considered to be at increased risk of, a particular disease or condition. Persons at risk of developing a particular disease or condition generally include those having a family history of the disease or condition and/or those who have been identified by genetic testing or screening to be particularly susceptible to developing the disease or condition.

Compound (I) and/or a pharmaceutically acceptable salt thereof may be used, for example, in the treatment of asthma, COPD, allergic rhinitis, allergic conjunctivitis, cancer, hepatitis B, hepatitis C, HIV, HPV, bacterial infections or a skin condition as listed hereinbefore (for example, atopic dermatitis, actinic keratosis, pre-cancerous skin lesions or cutaneous vial infections).

Thus, an aspect of the disclosure provides methods of treating and/or reducing the risk of asthma, COPD or allergic rhinitis comprising administering to a patient in need thereof a therapeutically effective amount of Compound (I) and/or a pharmaceutically acceptable salt thereof. As a further aspect of the disclosure, there is provided a method of treating and/or reducing the risk of asthma comprising administering to a patient in need thereof. Compound (I) and/or a pharmaceutically acceptable salt thereof. As a further aspect of the disclosure, there is provided a method of treating and/or reducing the risk of COPD comprising administering to a patient in need thereof a therapeutically effective amount of Compound (I) and/or a pharmaceutically acceptable salt thereof. As a further aspect of the disclosure, there is provided a method of treating and/or reducing the risk of allergic rhinitis comprising administering to a patient in need thereof a therapeutically effective amount of Compound (I) and/or a pharmaceutically acceptable salt thereof.

As a further aspect of the disclosure there is provided a method of treating and/or reducing the risk of a skin condition as hereinbefore described (for example atopic dermatitis, actinic keratosis, pre-cancerous lesions or cutaneous vial infections) comprising administering to a patient in need thereof a therapeutically effective amount of Compound (I) and/or a pharmaceutically acceptable salt thereof.

Compound (I) and/or a pharmaceutically acceptable salt thereof may also be useful as a vaccine adjuvant. As a further aspect of the disclosure, there is provided methods of treating and/or reducing the risk of a disease or condition as hereinbefore described comprising administering to a patient in need thereof a therapeutically effective amount of a vaccine in combination with Compound (I) and/or a pharmaceutically acceptable salt thereof.

As a further aspect of the disclosure there is provided the use of Compound (I) and/or a pharmaceutically acceptable salt thereof in the manufacture of a medicament for the treatment of asthma, COPD or allergic rhinitis. As a further aspect of the disclosure there is provided the use of a compound chosen from a compound of formula (I) and pharmaceutically acceptable salts thereof in the manufacture of a medicament for the treatment of a skin condition as hereinbefore described (for example atopic dermatitis, actinic keratosis, pre-cancerous lesions or cutaneous vial infections). As a further aspect of the disclosure there is provided the use of Compound (I) and/or a pharmaceutically acceptable salt thereof as a vaccine adjuvant in the manufacture of a vaccine for the treatment of a disease or condition.

The disclosure provides a method of treating an inflammatory disease in a patient suffering from, or at risk of, the disease, which comprises administering to the patient a therapeutically effective amount of Compound (I) and/or a pharmaceutically acceptable salt thereof.

The disclosure also provides a method of treating an airways disease, e.g. a reversible obstructive airways disease such as asthma, in a patient suffering from, or at risk of, the disease, which comprises administering to the patient a therapeutically effective amount of Compound (I) and/or a pharmaceutically acceptable salt thereof.

The disclosure still further provides a method of treating, or reducing the risk of, a disease or condition comprising or arising from abnormal cell growth (e.g. a cancer), which method comprises administering to a patient in need thereof a therapeutically effective amount of Compound (I) and/or a pharmaceutically acceptable salt thereof.

The disclosure still further provides a method of treating, or reducing the risk of, a skin disease or condition as hereinbefore described (for example atopic dermatitis, actinic keratosis, pre-cancerous lesions or cutaneous vial infections), which method comprises administering to a patient in need thereof a therapeutically effective amount of Compound (I) and/or a pharmaceutically acceptable salt thereof.

The disclosure still further provides a method of treating, or reducing the risk of, a disease or condition, which method comprises administering to a patient in need thereof a therapeutically effective amount of a vaccine and a salt of Compound (I) defined herein or a solvate of the salt.

The disclosure still further provides a method of increasing the response to a vaccine in a patient, which method comprises administering to a patient in need thereof a therapeutically effective amount of a vaccine and Compound (I) and/or a pharmaceutically acceptable salt thereof.

For the above-mentioned therapeutic uses, the dosage administered may vary with the mode of administration, the treatment desired, and the disorder indicated.

For example, if inhaled, the daily dosage of Compound (I) and/or a pharmaceutically acceptable salt thereof may range from 0.05 micrograms per kilogram body weight ($\mu g/kg$) to 100 micrograms per kilogram body weight ($\mu g/kg$). In some embodiments, the dosage may range from about 0.1 $\mu g/kg$ to about 100 $\mu g/kg$, such as a dose of about 0.1 $\mu g/kg$, 0.5 $\mu g/kg$, 1 $\mu g/kg$, 1.5 $\mu g/kg$, 2 $\mu g/kg$, 5 $\mu g/kg$, 10 $\mu g/kg$, 20 $\mu g/kg$, 50 $\mu g/kg$ and 100 $\mu g/kg$.

For example, if administered orally, the daily dosage of Compound (I) and/or a pharmaceutically acceptable salt thereof may range from 0.01 micrograms per kilogram body weight ($\mu g/kg$) to 100 milligrams per kilogram body weight ($mg/kg$). In some embodiments, the oral dosage may range from about 0.1 $\mu g/kg$ to about 100 $\mu g/kg$, such as a dose of about 1 $\mu g/kg$, 2 $\mu g/kg$, 5 $\mu g/kg$, 10 $\mu g/kg$, 20 $\mu g/kg$, 50 $\mu g/kg$ and 100 $\mu g/kg$.

The dosages mentioned herein refer to the dose of Compound (I) as a free base unless otherwise indicated. Accordingly, an equivalent dose of a particular salt will be higher because of the increased molecular weight of the salt compared to the free base.

The compounds disclosed herein may be used alone, but may also be administered in the form of a pharmaceutical composition in which Compound (I) and/or a pharmaceutically acceptable salt thereof is in association with at least one component chosen from pharmaceutically acceptable adjuvants, pharmaceutically acceptable diluents, and pharmaceutically acceptable carriers. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the concentration of Compound (I) and/or a pharmaceutically acceptable salt thereof of the pharmaceutical composition may range from 0.05% to 99%, such as from 0.05% to 80%, from 0.10% to 70%, and from 0.10% to 50% by weight relative to the total weight of the pharmaceutical composition. The concentrations mentioned herein refer to the concentration of Compound (I) as a free base unless otherwise indicated. An equivalent concentration of a particular salt can be calculated based on molecular weights.

The present disclosure also provides a pharmaceutical composition comprising Compound (I) and/or a pharmaceutically acceptable salt thereof in association with at least one component chosen from pharmaceutically acceptable adjuvants, pharmaceutically acceptable diluents, and pharmaceutically acceptable carriers.

The disclosure further provides a process for the preparation of a pharmaceutical composition disclosed herein, which comprises mixing Compound (I) and/or a pharmaceutically acceptable salt thereof with at least one component chosen from pharmaceutically acceptable adjuvants, pharmaceutically acceptable diluents, and pharmaceutically acceptable carriers.

The pharmaceutical compositions may be administered: topically (e.g. to the skin or to the lung and/or airways (by oral or nasal inhalation) administration) in the form, for example, of creams, solutions, suspensions, heptafluoroalkane (HFA) aerosols and dry powder formulations (for example, formulations in the inhaler device known as the Turbuhaler®); systemically, for example, by oral administration in the form, for example, of tablets, capsules, syrups, powders or granules; by parenteral administration in the form, for example, of solutions or suspensions; by subcutaneous administration; by rectal administration in the form, for example, of suppositories; or transdermally.

For oral administration, Compound (I) and/or a pharmaceutically acceptable salt thereof may be admixed with at least one additional compound chosen from adjuvants and carriers, for example, lactose, saccharose, sorbitol, and mannitol; starches, for example, potato starch, corn starch, and amylopectin; cellulose derivatives; binders, for example, gelatine and polyvinylpyrrolidone; and lubricants, for example, magnesium stearate, calcium stearate, polyethylene glycol, waxes, paraffin, and the like; and then optionally compressed into tablets. In some embodiments, the cores of the tablets, prepared as described above, may be coated with a concentrated sugar solution which may contain, for example, gum arabic, gelatin, talcum and/or titanium dioxide. Alternatively, the tablet may be coated with a suitable polymer dissolved in a readily volatile organic solvent.

For the preparation of soft gelatin capsules, Compound (I) and/or a pharmaceutically acceptable salt thereof may be admixed with, for example, a vegetable oil and/or polyethylene glycol. Hard gelatin capsules may contain granules of the compound disclosed herein using the above-mentioned excipients for tablets. Also liquid or semisolid formulations of the compound disclosed herein may be filled into hard gelatine capsules.

Liquid preparations for oral application may be in the form of syrups or suspensions, for example, solutions containing the compound disclosed herein, sugar as a balance and a mixture of ethanol, water, glycerol and propylene glycol. Optionally such liquid preparations may contain coloring agents, flavoring agents, saccharine and/or carboxymethylcellulose as a thickening agent or other excipients known to those skilled in the art.

Pharmaceutical Compositions for Administration by Inhalation

In some embodiments, the pharmaceutical composition is administered by inhalation (oral or nasal).

A pharmaceutical composition comprising Compound (I) and/or a pharmaceutically acceptable salt thereof may be administered using a suitable delivery device known in the art, for example, a dry powder inhaler, a metered dose inhaler, a nebuliser, or a nasal delivery device.

In some embodiments, the pharmaceutical composition is administered using a dry powder inhaler (DPI). The DPI may be "passive" or breath-actuated, or "active" where the powder is dispersed by some mechanism other than the patient's inhalation, for instance, an internal supply of compressed air. Passive dry powder inhalers may be single-dose, multiple unit dose or multidose (reservoir) inhalers. In single-dose inhalers, individual doses are provided, usually in the form of gelatin capsules, and may be loaded into the inhaler before use, examples of which include Spinhaler® (Aventis), Rotahaler® (GlaxoSmithKline), Aeroliser™ (Novartis), Inhalator® (Boehringer) and Eclipse (Aventis) devices. Multiple unit dose inhalers contain a number of individually packaged doses, such as multiple gelatine capsules and in blisters, examples of which include Diskhaler® (GlaxoSmithKline), Diskus® (GlaxoSmithKline) and Aerohaler® (Boehringer) devices. In multidose inhalers, drug is stored in a bulk powder reservoir from which individual doses are metered, examples of which include Turbuhaler® (AstraZeneca), Easyhaler (Orion), Novolizer (ASTA Medica), Clickhaler® (Innovata Biomed) and Pulvinal® (Chiesi) devices.

An inhalable pharmaceutical composition or dry powder formulation for use in a DPI can be prepared by mixing a finely divided active ingredient (having a mass median diameter generally equal to or less than 10 μm, such as equal to or less than 5 μm) with a carrier substance, for example, a mono-, di- or polysaccharide, a sugar alcohol, or another polyol. Suitable carriers may be sugars or sugar alcohols, for example, lactose, glucose, raffinose, melezitose, lactitol, maltitol, trehalose, sucrose, mannitol; and starch. The carrier particles may have a mass median diameter ranging from 20 μm to 1000 μm, such as from 50 μm to 500 μm. The powder mixture may then, for example, be dispensed into hard gelatine capsules, each containing a desired dose of the active ingredient(s).

Alternatively, an inhalable pharmaceutical composition may be prepared by processing a finely divided powder (e.g. comprising a finely divided active ingredient and finely divided carrier particles) into spheres that break up during the inhalation procedure. This spheronized powder may be filled into the drug reservoir of a multidose inhaler, for example, the Turbuhaler® in which a dosing unit meters the desired dose which is then inhaled by the patient.

Accordingly, the present disclosure also provides a dry powder inhaler, in particular a multiple unit dose dry powder inhaler, containing an inhalable pharmaceutical composition disclosed herein.

In some embodiments, a pharmaceutical composition comprising Compound (I) and/or a pharmaceutically acceptable salt thereof may be administered using a metered dose inhaler (MDI), such as a pressurized metered dose inhaler (pMDI). The pMDI may contain the active ingredient as a suitable solution or suspension in a pressurized container. The active ingredient(s) may be delivered by actuating a valve on the pMDI device. Actuation may be manual or breath actuated. In manually actuated pMDIs, the device may be actuated by the user as they inhale, for example by pressing a suitable release mechanism on the pMDI device. Breath actuated pMDIs may be actuated when the patient inhales through the mouthpiece of the pMDI. This can be advantageous as the actuation of the device is timed with the patient's inhalation and can result in a more consistent dosing of the active ingredient(s). An example of a pMDI device includes Rapihaler® (AstraZeneca).

An inhalable pharmaceutical composition for use in a pMDI can be prepared by dissolving or dispersing Compound (I) and/or a pharmaceutically acceptable salt thereof in a suitable propellant with or without additional excipients such as solvents (for example ethanol), surfactants, lubricants, preservatives and/or stabilizing agents. Suitable propellants include, for example, hydrocarbon, chlorofluorocarbon and hydrofluoroalkane (e.g. heptafluoroalkane) propellants, and mixtures of any such propellants. Suitable propellants may be, for example, P134a and P227, each of which may be used alone or in combination with other propellants and/or surfactants and/or other excipients. When a pharmaceutical composition comprising Compound (I) and/or a pharmaceutically acceptable salt thereof is used as a suspension, the compound(s) may be present in finely divided form (having a mass median diameter generally equal to or less than 10 μm, such as equal to or less than 5 μm).

In some embodiments, a pharmaceutical composition comprising Compound (I) and/or a pharmaceutically acceptable salt thereof may be administered using a metered dose inhaler in combination with a spacer. Suitable spacers are well known in the art and include, for example, Nebuchamber® (AstraZeneca) or Volumatic® (GSK).

In some embodiments, a pharmaceutical composition comprising Compound (I) and/or a pharmaceutically acceptable salt thereof may be administered using a nebuliser. Suitable nebulisers are well-known in the art.

An inhalable pharmaceutical composition for use in a nebuliser can be prepared by dispersing or dissolving Compound (I) and/or a pharmaceutically acceptable salt thereof in a suitable aqueous medium. The composition may also include, for example, suitable pH and/or tonicity adjusters, surfactants, and preservatives. In some embodiments, Compound (I) and/or a pharmaceutically acceptable salt thereof may be administered nasally as a spray from a suitable nasal delivery device, for example, a spray pump or an MDI adapted for nasal delivery. Alternatively, Compound (I) and/or a pharmaceutically acceptable salt thereof may be administered nasally as a powder using a suitable DPI device, for example Rhinocort® or Turbuhaler® (AstraZeneca).

A nasally inhalable pharmaceutical composition for use in a spray pump or an MDI nasal delivery device can be prepared by dispersing or dissolving the Compound (I) and/or a pharmaceutically acceptable salt thereof in a suitable aqueous medium similar to those described above for inhalation via an MDI device. Suitable dry powder compositions for nasal delivery are as hereinbefore described in relation to DPI delivery. To limit the penetration of the compound(s) into the lung and keep the compound(s) in the nasal cavity, the compound(s) may be used in large particle sizes, for example, with an average particle diameter greater than about 10 μm, for example, ranging from 10 μm to 50 μm.

Accordingly, the present disclosure also provides an inhaler device suitable for nasal administration (for example, a dry powder inhaler, in particular a multiple unit dose dry powder inhaler, or a pMDI inhaler) containing an inhalable pharmaceutical composition disclosed herein.

Pharmaceutical Compositions for External Topical Administration

When Compound (I) and/or a pharmaceutically acceptable salt thereof, is administered as an external topical pharmaceutical composition, suitable forms of the compositions may include, for example, ointments, lotions, creams, gels, tapes, transdermal patches, cataplasms, and powders for external administration.

Ointments, creams and gels may contain Compound (I) and/or a pharmaceutically acceptable salt thereof in an amount ranging from about 0.01% to about 10% by weight relative to the total weight of the composition, and may further comprise, for example, at least one additional excipient, for example, selected from thickening agents, aqueous or oily bases, gelling agents, and solvents. Suitable aqueous/oily bases may include, for example, water and/or oil such as liquid paraffin, a vegetable oil such as arachis oil or castor oil. Examples of suitable solvents include polyethylene glycol. Examples of suitable thickening and gelling agents include soft paraffin, aluminium stearate, cetostearic alcohol, polyethylene glycol, sheep fat, beeswax, carboxypolymethylene and cellulose derivatives, glyceryl monostearate and/or nonionic emulsifiers.

Lotions may contain Compound (I) and/or a pharmaceutically acceptable salt thereof in an amount ranging from about 0.01% to about 10% by weight relative to the total weight of the composition, and may further comprise, for example, at least one additional excipient, for example, selected from aqueous and oily bases, emulsifiers, stabilizers, dispersing agents, precipitation inhibitors, and thickening agents.

Powders for external use may contain Compound (I) and/or a pharmaceutically acceptable salt thereof in an amount ranging from 0.01% to about 10% by weight relative to the total weight of the composition, and may be formulated using a suitable powdery base such as talc, lactose and starch.

The pharmaceutical compositions for external topical administration may be particularly suitable for the treatment of skin conditions mentioned herein (for example, atopic dermatitis, actinic keratosis, pre-cancerous lesions or cutaneous vial infections).

Compound (I) and/or a pharmaceutically acceptable salt thereof may also be administered in conjunction with other compounds used for the treatment of the above conditions.

The present disclosure therefore further provides combination therapies wherein Compound (I) and/or a pharmaceutically acceptable salt thereof is administered concurrently or sequentially or as a combined preparation with at least one additional therapeutic agent in the methods of treating and/or reducing the risk of a disease or condition listed above.

For example, Compound (I) and/or a pharmaceutically acceptable salt thereof may be combined with at least one additional agent chosen from the agents listed below:

Non-steroidal anti-inflammatory agents (hereinafter NSAIDs) including, for example, non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine. Also disclosed are combinations comprising Compound (I) and/or a pharmaceutically acceptable salt thereof with at least one cytokine or agonist or antagonist of cytokine function (including agents that act on cytokine signaling pathways such as modulators of the SOCS system) including, for example, alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

Also disclosed are combinations comprising Compound (I) and/or a pharmaceutically acceptable salt thereof with at least one monoclonal antibody targeting B-Lymphocyte (such as CD20 (rituximab), MRA-aILI6R and T-Lymphocytes, CTLA4-Ig (abatacept), HuMax II-15).

Compound (I) and/or a pharmaceutically acceptable salt thereof may be in combination with at least one modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

Compound (I) and/or a pharmaceutically acceptable salt thereof may be in combination with at least one inhibitor of matrix metalloprotease (MMPs), i.e., stromelysins, collagenases, gelatinases, and aggrecanases; especially collagenase-1 (MMP-1), collagenase-2 (MMP-8), collagenase-3 (MMP-13), stromelysin-1 (MMP-3), stromelysin-2 (MMP-10), stromelysin-3 (MMP-11), MMP-9 and MMP-12, including agents such as doxycycline.

Compound (I) and/or a pharmaceutically acceptable salt thereof may be in combination with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

Compound (I) and/or a pharmaceutically acceptable salt thereof may be in combination with a receptor antagonist for leukotrienes (LT) B4, LTC4, LTD4, and LTE4, selected from phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

Compound (I) and/or a pharmaceutically acceptable salt thereof may be in combination with a phosphodiesterase (PDE) inhibitor such as a methylxanthanine including theophylline and aminophylline, a selective PDE isoenzyme inhibitor including a PDE4 inhibitor, an inhibitor of the isoform PDE4D, and an inhibitor of PDE5.

Compound (I) and/or a pharmaceutically acceptable salt thereof may be in combination with at least one histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

Compound (I) and/or a pharmaceutically acceptable salt thereof may be in combination with at least one proton pump inhibitor (such as omeprazole) and/or at least one gastroprotective histamine type 2 receptor antagonist.

Compound (I) and/or a pharmaceutically acceptable salt thereof may be in combination with at least one antagonist of the histamine type 4 receptor.

Compound (I) and/or a pharmaceutically acceptable salt thereof may be in combination with at least one alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

Compound (I) and/or a pharmaceutically acceptable salt thereof may be in combination with at least one anticholinergic agents including muscarinic receptor (M1, M2, and M3) antagonist such as atropine, hyoscine, glycopyrrrolate, ipratropium bromide, tiotropium bromide, oxitropium bromide, pirenzepine, telenzepine, tolterodine, and aclidinium bromide.

Compound (I) and/or a pharmaceutically acceptable salt thereof may be in combination with at least one beta-adrenoceptor agonist (including beta receptor subtypes 1-4) such as isoprenaline, salbutamol, formoterol, salmeterol, terbutaline, orciprenaline, bitolterol mesylate, pirbuterol, and chiral enantiomers thereof, indacaterol, milveterol, carmoterol, olodaterol, (previously known as BI 1744 CL), for example as the hydrochloride salt, vilanterol (previously known as GW642444), for example as the trifenatate (triphenylacetete) salt.

Compound (I) and/or a pharmaceutically acceptable salt thereof may be in combination with at least one chromone, such as sodium cromoglycate and nedocromil sodium.

Compound (I) and/or a pharmaceutically acceptable salt thereof may be in combination with at least one glucocorticoid, such as flunisolide, triamcinolone acetonide, beclomethasone dipropionate, budesonide, fluticasone propionate, fluticasone furoate, ciclesonide and mometasone furoate.

Compound (I) and/or a pharmaceutically acceptable salt thereof may be in combination with at least one agent that modulates a nuclear hormone receptor such as PPARs.

Compound (I) and/or a pharmaceutically acceptable salt thereof may be in combination with at least one immunoglobulin (Ig) or Ig preparation or at least one antagonist or antibody modulating Ig function such as anti-IgE (for example omalizumab).

Compound (I) and/or a pharmaceutically acceptable salt thereof may be in combination with at least one other systemic or topically-applied anti-inflammatory agent, such as thalidomide or a derivative thereof, a retinoid, dithranol and calcipotriol.

Compound (I) and/or a pharmaceutically acceptable salt thereof may be in combination with at least one combination of aminosalicylates and sulfapyridine such as sulfasalazine, mesalazine, balsalazide, and olsalazine; and immunomodulatory agents such as the thiopurines, and corticosteroids such as budesonide.

Compound (I) and/or a pharmaceutically acceptable salt thereof may be in combination with at least one antibacterial agent such as a penicillin derivative, a tetracycline, a macrolide, a beta-lactam, a fluoroquinolone, metronidazole, an inhaled aminoglycoside; at least one antiviral agent including acyclovir, famciclovir, valaciclovir, ganciclovir, cidofovir, amantadine, rimantadine, ribavirin, zanamavir and oseltamavir; at least one protease inhibitor such as indinavir, nelfinavir, ritonavir, and saquinavir; at least one nucleoside reverse transcriptase inhibitor such as didanosine, lamivudine, stavudine, zalcitabine or zidovudine; and/or at least one non-nucleoside reverse transcriptase inhibitor such as nevirapine or efavirenz.

Compound (I) and/or a pharmaceutically acceptable salt thereof may be in combination with at least one cardiovascular agent such as a calcium channel blocker, at least one beta-adrenoceptor blocker, at least one angiotensin-converting enzyme (ACE) inhibitor, at least one angiotensin-2 receptor antagonist; at least one lipid lowering agent such as a statin or a fibrate; at least one modulator of blood cell morphology such as pentoxyfylline; at least one thrombolytic, or at least one anticoagulant such as a platelet aggregation inhibitor.

Compound (I) and/or a pharmaceutically acceptable salt thereof may be in combination with at least one CNS agent such as an antidepressant (such as sertraline), at least one anti-Parkinsonian drug (such as deprenyl, L-dopa, ropinirole, pramipexole, at least one MAOB inhibitor such as selegine and rasagiline, at least one comP inhibitor such as tasmar, at least one A-2 inhibitor, at least one dopamine reuptake inhibitor, at least one NMDA antagonist, at least one nicotine agonist, at least one dopamine agonist or at least one inhibitor of neuronal nitric oxide synthase), or at least one anti-Alzheimer's drug such as donepezil, rivastigmine, tacrine, at least one COX-2 inhibitor, propentofylline or metrifonate.

Compound (I) and/or a pharmaceutically acceptable salt thereof may be in combination with at least one agent for the treatment of acute or chronic pain, such as a centrally or peripherally-acting analgesic (for example an opioid or derivative thereof), carbamazepine, phenyloin, sodium valproate, amitryptiline or other antidepressant agents, paracetamol, or at least one non-steroidal anti-inflammatory agent.

Compound (I) and/or a pharmaceutically acceptable salt thereof may be in combination with at least one parenterally or topically-applied (including inhaled) local anaesthetic agent such as lignocaine or a derivative thereof.

Compound (I) and/or a pharmaceutically acceptable salt thereof may be in combination with at least one anti-osteoporosis agent including a hormonal agent such as raloxifene, or at least one biphosphonate such as alendronate.

Compound (I) and/or a pharmaceutically acceptable salt thereof may be in combination with at least one
 (i) tryptase inhibitor;
 (ii) platelet activating factor (PAF) antagonist;
 (iii) interleukin converting enzyme (ICE) inhibitor;
 (iv) IMPDH inhibitor;
 (v) adhesion molecule inhibitors including VLA-4 antagonist;
 (vi) cathepsin;
 (vii) kinase inhibitor such as an inhibitor of tyrosine kinase (such as Btk, Itk, Jak3 or MAP, for example gefitinib or imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase);
 (viii) glucose-6 phosphate dehydrogenase inhibitor;
 (ix) kinin-B.sub1.- or B.sub2.-receptor antagonist;
 (x) anti-gout agent, for example colchicine;
 (xi) xanthine oxidase inhibitor, for example allopurinol;
 (xii) uricosuric agent, for example probenecid, sulfinpyrazone or benzbromarone;
 (xiii) growth hormone secretagogue;
 (xiv) transforming growth factor (TGFβ);
 (xv) platelet-derived growth factor (PDGF);
 (xvi) fibroblast growth factor for example basic fibroblast growth factor (bFGF);
 (xvii) granulocyte macrophage colony stimulating factor (GM-CSF);
 (xviii) capsaicin cream;
 (xix) tachykinin NK.sub1. or NK.sub3. receptor antagonist such as NKP-608C, SB-233412 (talnetant) or D-4418;
 (xx) elastase inhibitor such as UT-77 or ZD-0892;
 (xxi) TNF-alpha converting enzyme inhibitor (TACE);
 (xxii) induced nitric oxide synthase (iNOS) inhibitor;
 (xxiii) chemoattractant receptor-homologous molecule expressed on TH2 cells, (such as a CRTH2 antagonist);
 (xxiv) inhibitor of P38;
 (xxv) agent modulating the function of Toll-like receptors (TLR),
 (xxvi) agent modulating the activity of purinergic receptors such as P2x7; or
 (xxvii) inhibitor of transcription factor activation such as NFkB, API, or STATS.

Compound (I) and/or a pharmaceutically acceptable salt thereof may be in combination with at least one existing therapeutic agent for the treatment of cancer. For example, suitable at least one existing therapeutic agent may include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213; an agent used in antisense therapy, for example one directed to one of the targets listed above, such as ISIS 2503, an anti-ras antisense;

(vii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (viii) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

The present disclosure further provides a pharmaceutical composition (for example, for use as a medicament for the treatment of one of the diseases or conditions listed herein such as COPD, asthma or allergic rhinitis) comprising Compound (I) and/or a pharmaceutically acceptable salt thereof as hereinbefore defined and at least one agent independently selected from:

a) PDE4 inhibitors including an inhibitor of the isoform PDE4D;
b) β-adrenoceptor agonists such as metaproterenol, isoproterenol, isoprenaline, albuterol, salbutamol, formoterol, salmeterol, terbutaline, orciprenaline, bitolterol mesylate, pirbuterol, indacaterol and carmoterol;
c) muscarinic receptor antagonists (for example a M1, M2 or M3 antagonist, such as a selective M3 antagonist) such as ipratropium bromide, tiotropium bromide, oxitropium bromide, pirenzepine, telenzepine and tolterodine;
d) modulators of chemokine receptor function (such as a CCR1 or CCR8 receptor antagonist);
e) inhibitors of kinase function;
f) non-steroidal glucocorticoid receptor agonists;
g) steroidal glucocorticoid receptor agonists;
h) protease inhibitors (such as a MMP12 or MMP9 inhibitor); and
i) antiproliferative agents.

The present disclosure still further provides a kit comprising at least one first active ingredient which is Compound (I) and/or a pharmaceutically acceptable salt thereof as hereinbefore defined and a preparation of at least one second active ingredient selected from:

a) PDE4 inhibitors including inhibitors of the isoform PDE4D;
b) β-adrenoceptor agonists such as metaproterenol, isoproterenol, isoprenaline, albuterol, salbutamol, formoterol, salmeterol, terbutaline, orciprenaline, bitolterol mesylate, pirbuterol, indacaterol and carmoterol;
c) muscarinic receptor antagonists (for example a M1, M2 or M3 antagonist, such as a selective M3 antagonist) such as ipratropium bromide, tiotropium bromide, oxitropium bromide, pirenzepine, telenzepine and tolterodine;
d) modulators of chemokine receptor function (such as a CCR1 or CCR8 receptor antagonist);
e) inhibitors of kinase function;
f) non-steroidal glucocorticoid receptor agonists;
g) steroidal glucocorticoid receptor agonists;
h) protease inhibitors (such as a MMP12 or MMP9 inhibitor); and
i) antiproliferative agents;

and instructions for the simultaneous, sequential or separate administration of the preparations to a patient in need thereof.

EXAMPLES

Figure 1:
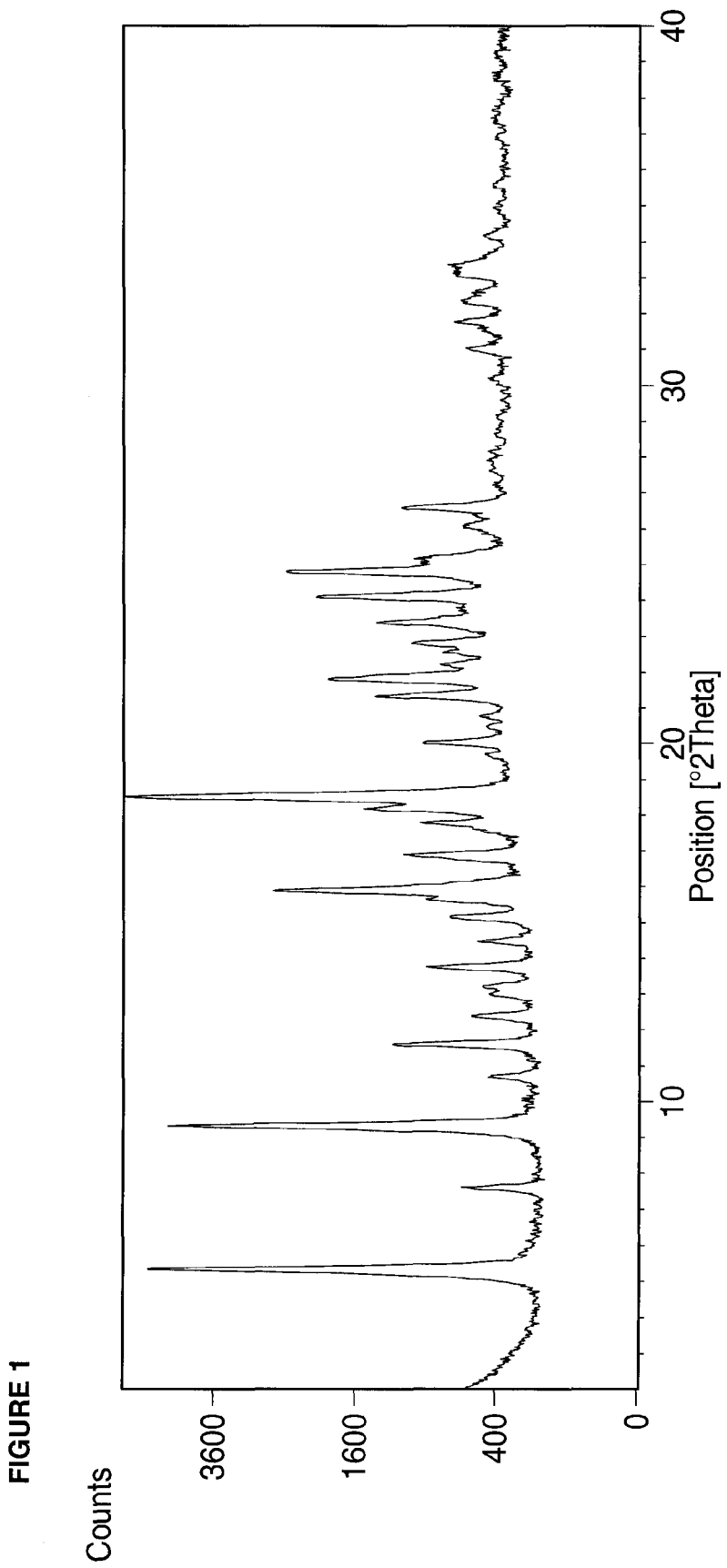
FIG. 1 is an X-ray powder diffraction pattern of Compound (I) Form A measured at a wavelength of 1.5418 Å. The x-axis shows the 2-theta value and the y-axis shows the intensity.

The present disclosure will now be further illustrated by reference to the following examples in which, unless stated otherwise:

(i) Temperatures are given in degrees Celsius (° C.); operations were carried out at room or ambient temperature ranging from 18° C. to 25° C.

(ii) In general, the course of reactions was followed by HPLC and reaction times are given for illustration only.

(iii) Yields are given for illustration only and are not necessarily those which can be obtained by diligent process development; preparations were repeated if more material was required.

(iv) Chemical symbols have their usual meanings; SI units and symbols are used.

(v) Solvent ratios are given in volume: volume (v/v) terms.

(vi) Unless stated otherwise, starting materials were commercially available.

(vii) Unless stated otherwise, example names have been generated using the IUPAC naming function of ACD Labs Version 10 (Advanced Chemistry Development, Inc.).

General Methods $^1$H NMR spectra were recorded at 298K on a Bruker Avance-III 500 spectrometer, operating at 500 MHz.

"RPHPLC" means reversed phase preparative HPLC using Waters Symmetry C8, Xterra, XBridge or Phenomenex Gemini columns, using acetonitrile and either aqueous ammonium acetate, ammonia, formic acid or trifluoroacetic acid as buffer where appropriate. Column chromatography was carried out on silica gel. The term "passed through an SCX" means the mixture was absorbed on SCX and eluted with an appropriate solvent such as methanol or acetonitrile, and then the free base product was eluted with aqueous ammonia/methanol.

Mass spectra were run on an Agilent 100 HPLCMS equipped with a multimode source.

X-Ray Powder Diffraction (XRPD) patterns were measured using a PANalytical X'Pert machine in 2θ-θ configuration or a PANalytical Cubix machine in θ-θ configuration over the scan range from 2° to 40° 2θ with 100-second exposure per 0.02° increment. The X-rays were generated by a copper long-fine focus tube operated at 45 kV and 40 mA. The wavelength of the copper X-rays was 1.5418 Å. The Data was collected on zero background holders on which about 2 mg of the compound was placed. The holder was made from a single crystal of silicon, which had been cut along a non-diffracting plane and then polished on an optically flat finish. The X-rays incident upon this surface were negated by Bragg extinction.

Differential Scanning calorimetry (DSC) thermograms were measured using a TA Q2000 Differential Scanning calorimeter, with aluminium pans. The sample weights varied between 0.5 mg to 5 mg. The procedure was carried out under a flow of nitrogen gas (50 ml/min) and the temperature studied from 0° to 300° C. at a constant rate of temperature increase of 10° C. per minute.

Thermogravimetric Vapour Sorption (TGA) thermograms were measured using a TA Q500 Thermogravimetric Analyser, with platinum pans. The sample weights varied between 1 mg and 5 mg. The procedure was carried out under a flow of nitrogen gas (60 ml/min) and the temperature studied from room temperature to 300° C. at a constant rate of temperature increase of 10° C. per minute.

Gravimetric Vapour Sorption (GVS) profiles were measured using a TA Instruments Q5000SA instrument. Approximately 1 mg to 5 mg of the solid sample was placed into a metal vessel, and the weight of the sample was recorded during a dual cycle step method (40 to 90 to 0 to 90 to 0% relative humidity (RH), in steps of 10% RH).

ABBREVIATIONS

The following abbreviations have been used.
aq. aqueous
DCM: dichloromethane
DMF: N,N-dimethylformamide
EtOAc: ethyl acetate
hrs: hours
MeCN: acetonitrile
MeOH: methanol
MS: mass spectrometry
mins: minutes
rt: room temperature

Example 1

Methyl (3-{[{4-[4-amino-2-(ethoxymethyl)-1H-imidazo[4,5-c]quinolin-1-yl]butyl}(N,N-diethylglycyl)amino]methyl}phenyl)acetate

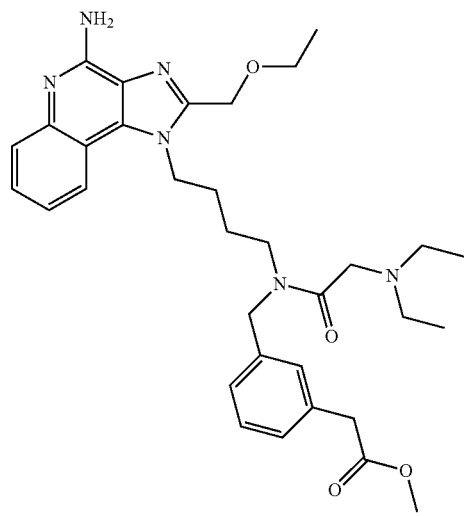 [SMILES: CCOCc1nc2c(N)nc3ccccc3c2n1CCCCN(Cc1cccc(CC(=O)OC)c1)C(=O)CN(CC)CC]

A suspension of methyl {3-[({4-[4-amino-2-(ethoxymethyl)-1H-imidazo[4,5-c]quinolin-1-yl]butyl}amino)methyl]phenyl}acetate (507 mg) in MeCN (8 mL) was treated dropwise with chloroacetyl chloride (94 µL), and the mixture stirred at rt for 1 hour. DMF (3 mL) was added and the solvent evaporated under reduced pressure to remove the MeCN. The mixture was cooled in an ice bath and diethylamine (390 mg) was added then stirred for 18 hours at rt. The solution was then partitioned between EtOAc and brine, the organics were combined, dried and solvent removed. The crude product was purified by RPHPLC, and the pure fractions were partially evaporated down to remove the MeCN, and the remaining water mixture cooled and neutralised by addition of solid sodium bicarbonate and sodium chloride, the mixture then extracted with DCM. The combined organics were dried, filtered and the solvent removed under reduced pressure to yield the title compound as a solid (350 mg); MS multimode (+) 589; $^1$H NMR (500 MHz, DMSO, 91° C.) δ 7.98 (d, 1H), 7.63 (d, 1H), 7.43 (t, 1H), 7.25 (d, 2H), 7.15-7.06 (m, 3H), 6.19 (s, 2H), 4.73 (s, 2H), 4.63-4.47 (m, 4H), 3.62-3.54 (m, 7H), 3.34 (s, 2H), 3.21 (s, 2H), 2.50-2.45 (m, 4H), 1.83 (s, 2H), 1.67 (s, 2H), 1.15 (t 3H), 0.87 (t, 6H).

The methyl {3-[({4-[4-amino-2-(ethoxymethyl)-1H-imidazo[4,5-c]quinolin-1-yl]butyl}amino)methyl]phenyl}acetate used as the starting material was prepared as follows.

(i) tert-butyl {4-[(3-nitroquinolin-4-yl)amino]butyl}carbamate

To a suspension of 3-nitroquinolin-4-ol (60 g) in DCM (600 mL) and DMF (18 mL), thionyl chloride (29.9 mL) was added drop wise over 10 mins and then heated at 40° C. for 2 hours. The mixture was evaporated to dryness and the solid residue was added to a stirred solution of tert-butyl 4-aminobutylcarbamate (65.3 g) and triethylamine (176 mL) in DCM (1000 mL) at 0° C. The mixture was stirred at rt for 2 hours, then evaporated to dryness and the residue triturated with water. Drying in an oven gave the subtitle compound as a solid (110 g); MS multimode (+) 361;

(ii) tert-butyl {4-[(3-aminoquinolin-4-yl)amino]butyl}carbamate

Nickel(II) chloride hexahydrate (18.4 g) was dissolved in MeOH (360 mL) and cooled to 5° C. Sodium borohydride (2.9 g) was added followed by the product from step (i) (28 g). More sodium borohydride (11.7 g) was added slowly keeping the temperature below 23° C. then stirred for 1 h. The reaction mixture was filtered through celite and the filtrate was poured into sodium bicarbonate solution (300 mL). The solvent was reduced by half and then extracted with chloroform, combined organics were dried, and solvent removed to give the subtitle compound as a solid (22 g); MS multimode (+) 331

(iii) 2-ethoxyacetyl chloride

To a solution of 2-ethoxyacetic acid (25 g) in DCM (300 mL) dicyclohexylamine (47.4 mL) was added dropwise, and stirred for one hour. Thionyl chloride (19.2 mL) was then added dropwise and the mixture stirred for 3 hours. The reaction was diluted with ether (600 mL) and filtered, the filtrate was evaporated to dryness to give the subtitle compound as a pale brown oil (30 g).

(iv) tert-butyl {4-[2-(ethoxymethyl)-1H-imidazo[4,5-c]quinolin-1-yl]butyl}carbamate The product from step (iii) (10.38 g) was added dropwise to a solution of the product from step (ii) (28 g) at 0° C. in DCM (400 mL) and triethylamine (11.81 mL) over 1 hour then heated under reflux overnight. The reaction was cooled to rt and the solution washed with saturated sodium hydrogen carbonate, dried and solvent removed. The crude product was purified on silica to give the subtitle compound as a solid (26 g); MS multimode (+) 399.

(v) 1-(4-aminobutyl)-2-(ethoxymethyl)-1H-imidazo[4,5-c]quinolin-4-amine

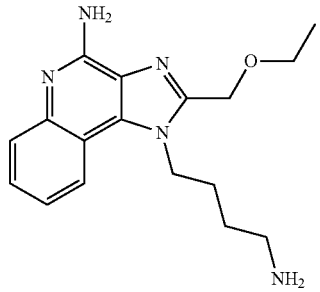 [SMILES: CCOCc1nc2c(N)nc3ccccc3c2n1CCCCN]

A solution of the product from step (iv) (3 g) in MeOH (100 mL) was treated with HCl in dioxane (14.51 mL, 4 M) and the reaction mixture allowed to stand at 20° C. for 3 hours. The solvent was evaporated under reduced pressure and the residue was azeotroped with MeCN to give the solid hydrochloride salt. This was dissolved in MeOH (100 mL) and passed through a SCX cartridge eluting with 10% NH$_3$/MeOH. The solvent was evaporated under reduced pressure and the residue azeotroped with MeCN to give the subtitle compound as a solid (2.3 g); MS multimode (+) 314.

(vi) methyl {3-[({4-[4-amino-2-(ethoxymethyl)-1H-imidazo[4,5-c]quinolin-1-yl]butyl}amino)methyl]phenyl}acetate

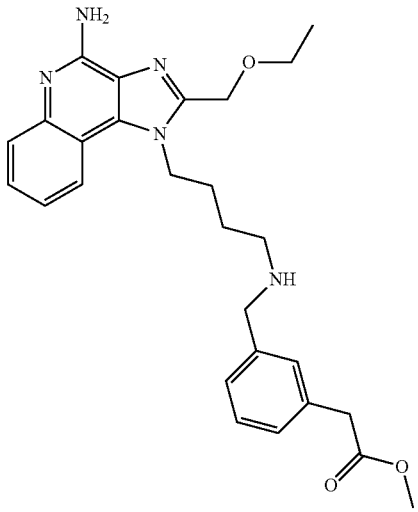 [SMILES: CCOCc1nc2c(N)nc3ccccc3c2n1CCCCNCc1cccc(CC(=O)OC)c1]

A solution of the product from step (v) (1.1 g) in MeOH (30 mL) was treated with acetic acid (0.37 mL) followed by methyl 2-(3-formylphenyl)acetate (0.61 g) and was stirred at rt for 20 mins and then cooled in an ice bath. Sodium cyanoborohydride (0.41 g) was added and the reaction mixture was stirred at rt for 3 hours. The solvent was evaporated under reduced pressure and the residue partitioned between EtOAc and sodium bicarbonate solution. The organic layer was evaporated under reduced pressure and the crude product was purified by silica chromatography to give the subtitle compound as a solid (1.16 g); MS multimode (+) 476; $^1$H NMR (500 MHz, DMSO) δ 9.41 (s, 2H), 8.95 (s, 2H), 8.74 (dd, 1H), 8.17 (dd, 1H), 7.75 (dd, 1H), 7.46-7.28 (m, 4H), 4.94-4.74 (m, 4H), 4.14 (s, 2H), 3.68 (s, 2H), 3.65-3.35 (m, 5H), 3.00 (s, 2H), 2.04-1.87 (m, 2H), 1.81-1.67 (m, 2H), 1.18 (t, 3H).

The compound prepared in Example 1 was crystalline (Compound (I) Form A) and provided the XRPD pattern shown in FIG. 1 when measured at a wavelength of 1.5418 Å. The most prominent peaks of the XRPD pattern for Compound (I) Form A are shown in Table 1 in the description.

Figure 2:
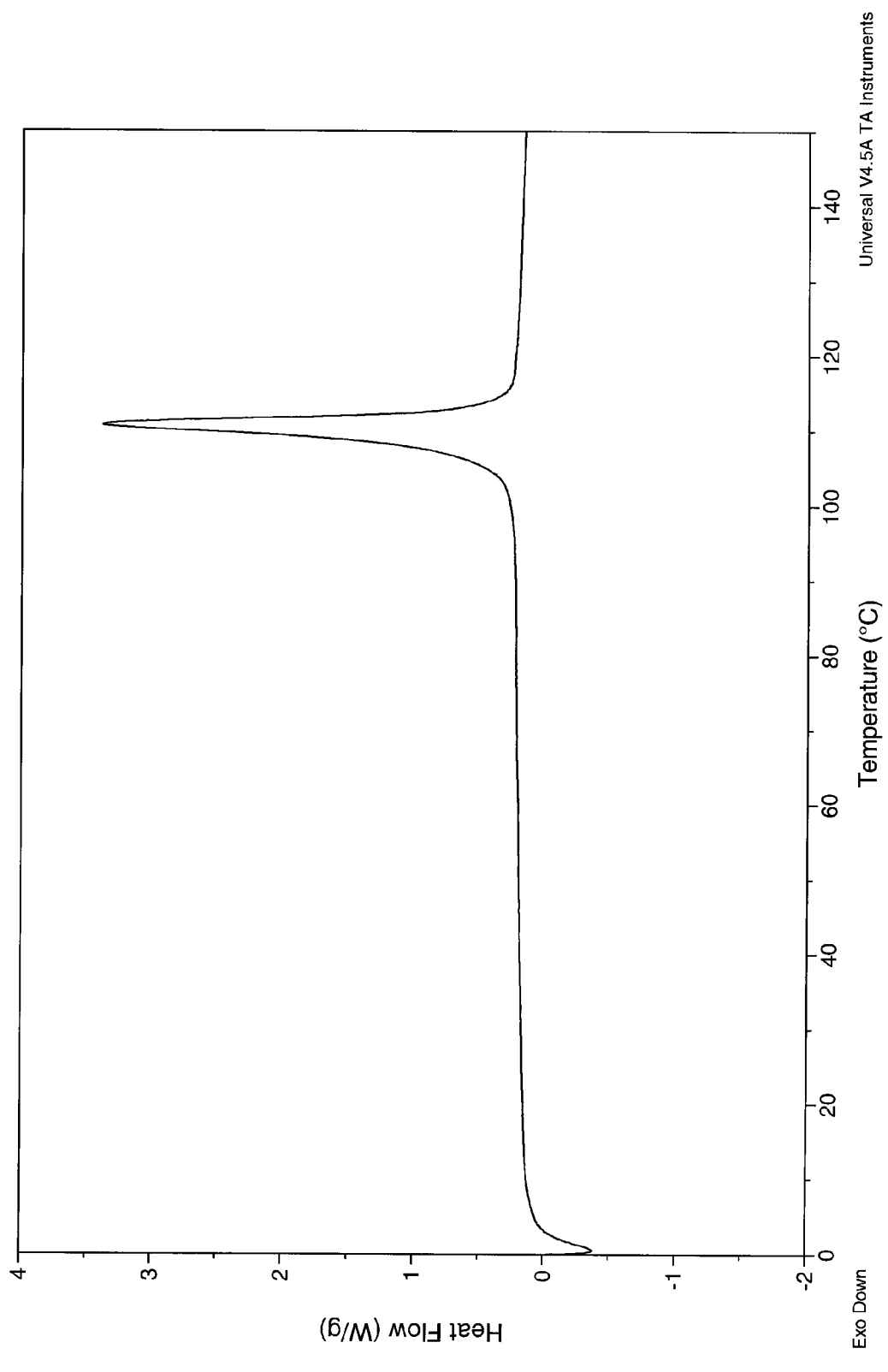
FIG. 2 is a differential scanning calorimetry (DSC) trace for Compound (I) Form A. The x-axis shows the temperature (° C.) and the y-axis shows the heat flow (watts/g).

When heated in a Differential Scanning calorimeter (DSC) (conditions as described in the Examples section) Compound (I) Form A exhibited a melting endotherm with an onset temperature at about 108° C., as illustrated in FIG. 2.

Thermogravimetric Vapour Sorption (TGA) thermograms on Compound (I) Form A showed no mass loss prior to the melting of the compound.

Gravimetric Vapour Sorption (GVS) profiles on Compound (I) Form A showed a mass increase at 80% relative humidity of 0.5% in cycle 1 and 0.64% in cycle 2.

Comparative Example 1

Methyl 2-(3-((N-(3-(4-amino-2-(ethoxymethyl)-1H-imidazo[4,5-c]quinolin-yl)propyl)-2-(dimethylamino)acetamido)methyl)phenyl)acetate

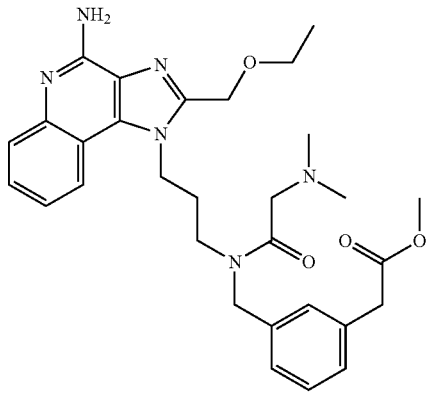 [SMILES: CCOCc1nc2c(N)nc3ccccc3c2n1CCCN(Cc1cccc(CC(=O)OC)c1)C(=O)CN(C)C]

The compound may be prepared using the method described in Example 7 of PCT Publication No. WO 2008/135791.

Biological Activity
Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) was controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the test compound prepared above in the presence of 0.1% (v/v) dimethylsulfoxide (DMSO). Concentration dependent induction of SEAP production by compounds was expressed as the concentration of compound which produced half of the maximal level of SEAP induction for that compound (pEC50).

Compound (I) (Example 1) gave a mean pEC50 of 7.4 (n=7).

Comparative Example 1 gave a mean pEC50 of 6.4 (n=4).

Cynomolgous Monkey Plasma Stability

To determine the half life of the test compound in cynomolgous monkey plasma, incubations were performed at 37° C. in a shaking water bath. The test compound (5 μL of a 100 μM stock in MeCN) was spiked into 0.495 mL plasma to give a final incubation concentration of 1 μM. Aliquots (50 μL) were withdrawn at various time points (typically 0, 20 and 40 sec, 1, 2, 3, 5 and 10 mins) and quenched into MeCN (300 μL) followed by analysis for parent compound by LC-MS-MS (MRM mode). The half life was calculated from the decline of test compound peak area over time Compound (I) (Example 1) gave a mean half life of 1.2 minutes (n=6)

Comparative Example 1 gave a half life of 11 minutes (n=1)

Human Plasma Stability

To determine the half life of the test compound in human plasma, incubations were performed at 37° C. in a shaking water bath. Compound (5 μL of a 100 μM stock in MeCN) was spiked into 0.495 mL plasma to give a final incubation concentration of 1 μM. Aliquots (50 μL) were withdrawn at various time points (typically 0, 20 and 40 sec, 1, 2, 3, 5 and 10 mins) and quenched into MeCN (300 μL) followed by analysis for parent compound by LC-MS-MS (MRM mode). The half life was calculated from the decline of test compound peak area over time.

Example 1 (Compound (I)) gave a mean half life of 0.3 minutes (n=8)

Comparative Example 1 gave a half life of 0.7 minutes (n=1)

What is claimed is:

1. A compound of formula (I) and/or pharmaceutically acceptable salts thereof:

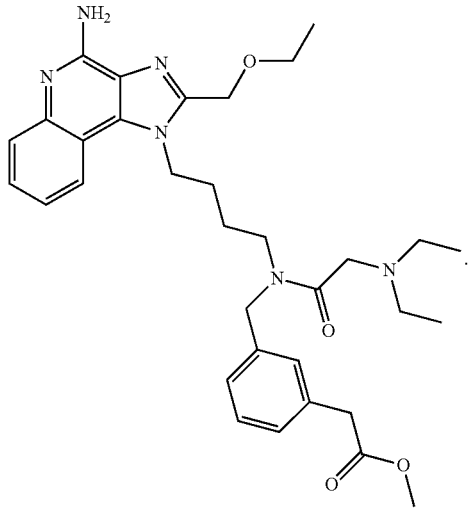

(I)

2. The compound according to claim 1, wherein said compound of formula (I) is in the form of a free base.

3. The compound according to claim 1, wherein said compound of formula (I) is in the form of a pharmaceutically acceptable salt.

4. The compound according to claim 1, wherein said compound of formula (I) is Form A.

5. A pharmaceutical composition comprising a compound according to claim 1 and/or pharmaceutically acceptable salts thereof and at least one component chosen from pharmaceutically acceptable adjuvants, pharmaceutically acceptable diluents, and pharmaceutically acceptable carriers.

6. The pharmaceutical composition according to claim 5, in a form for topical administration, systemic administration, parenteral administration, subcutaneous administration, rectal administration, or transdermal administration.

7. The pharmaceutical composition according to claim 5, further comprising at least one additional therapeutic agent.

8. The pharmaceutical composition according to claim 7, wherein said at least one additional therapeutic agent is chosen from:
    a) PDE4 inhibitors;
    b) β-adrenoceptor agonists;
    c) muscarinic receptor antagonists;
    d) modulators of chemokine receptor function;
    e) inhibitors of kinase function;
    f) non-steroidal glucocorticoid receptor agonists;
    g) steroidal glucocorticoid receptor agonists;
    h) protease inhibitors; and
    i) antiproliferative agents.

9. A process for the preparation of a compound according to claim 1 comprising:
    a) reacting a compound of formula (II) or a salt thereof:

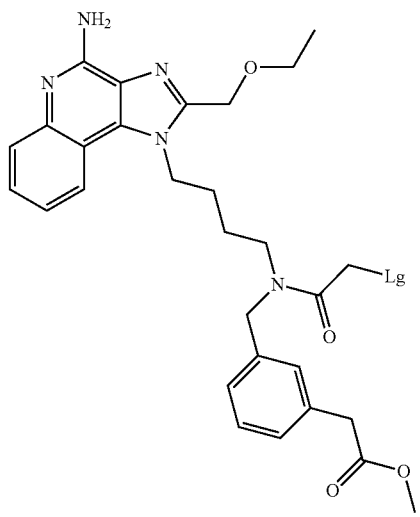

(II)

wherein Lg is a leaving group chosen from halo, mesylate, triflate, besylate, and tosylate,
    with diethylamine to a form compound of formula (I); or
    b) coupling a compound of formula (III) or a salt thereof:

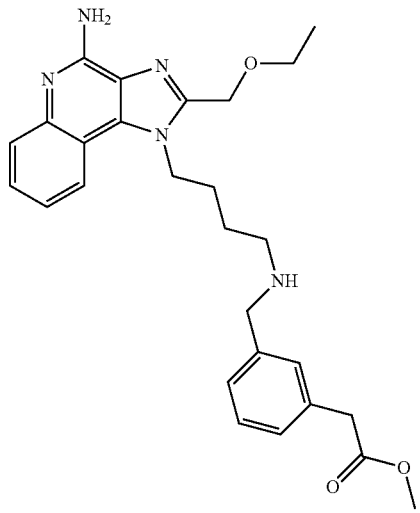

(III)

with 2-(diethylamino)acetic acid or a salt thereof to form a compound of formula (I); and
    c) optionally forming a pharmaceutically acceptable salt of the compound of formula (I).

10. A kit comprising, as at least one first active ingredient, a compound of formula (I) and/or a pharmaceutically acceptable salt thereof:

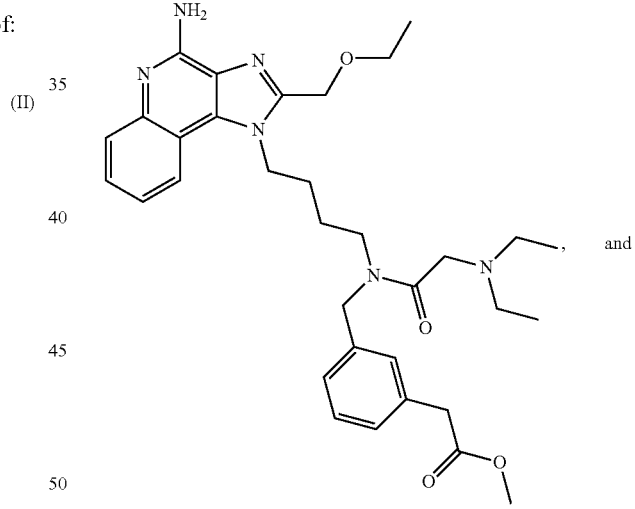

(I)

at least one second active ingredient chosen from:
    a) PDE4 inhibitors;
    b) β-adrenoceptor agonists;
    c) muscarinic receptor antagonists;
    d) modulators of chemokine receptor function;
    e) inhibitors of kinase function;
    f) non-steroidal glucocorticoid receptor agonists;
    g) steroidal glucocorticoid receptor agonists;
    h) protease inhibitors; and
    i) antiproliferative agents,
and instructions for the simultaneous, sequential or separate administration of the active ingredients to a patient in need thereof.

11. A compound chosen from a compound of formula (II) and/or salts thereof:

(II)
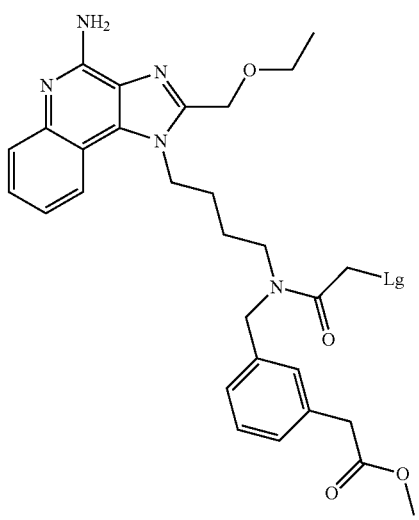
wherein Lg is a leaving group chosen from halo, mesylate, triflate, besylate, and tosylate.
12. A compound chosen from a compound of formula (III) and/or salts thereof:
(III)
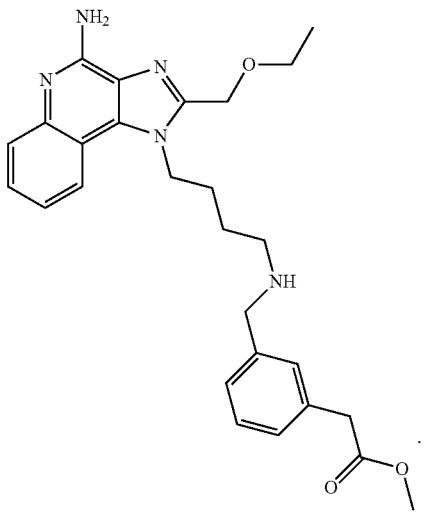
* * * * *